US008685399B2

(12) United States Patent
Hoff et al.

(10) Patent No.: US 8,685,399 B2
(45) Date of Patent: Apr. 1, 2014

(54) PAX 5 MONOCLONAL ANTIBODY

(75) Inventors: Kirsten Damgaard Hoff, Måløv (DK); Jakob O. Gjørret, Holte (DK); Kurt Pii, Farum (DE); Sussie Steen Jensen, Glostrup (DK); Henrik Winther, Hellerup (DK)

(73) Assignee: Dako Denmark A/S (DK)

( * ) Notice: Subject to any disclaimer, the term of this patent is extended or adjusted under 35 U.S.C. 154(b) by 10 days.

(21) Appl. No.: 13/001,965

(22) PCT Filed: Jun. 25, 2009

(86) PCT No.: PCT/DK2009/000156
§ 371 (c)(1),
(2), (4) Date: Mar. 31, 2011

(87) PCT Pub. No.: WO2010/006601
PCT Pub. Date: Jan. 21, 2010

(65) Prior Publication Data
US 2011/0177077 A1 Jul. 21, 2011

Related U.S. Application Data

(60) Provisional application No. 61/076,793, filed on Jun. 30, 2008.

(30) Foreign Application Priority Data

Jun. 30, 2008 (DK) ................................ 2008 00903

(51) Int. Cl.
| | | |
|---|---|---|
| *A61K 39/395* | (2006.01) | |
| *A61K 38/00* | (2006.01) | |
| *A61K 38/04* | (2006.01) | |
| *C07K 5/00* | (2006.01) | |
| *C07K 7/00* | (2006.01) | |
| *C07K 16/00* | (2006.01) | |
| *C12P 21/08* | (2006.01) | |
| *G01N 33/53* | (2006.01) | |
| *G01N 33/566* | (2006.01) | |

(52) U.S. Cl.
USPC ........ 424/138.1; 530/326; 530/325; 530/324; 530/329; 530/328; 530/327; 530/387.7; 530/330; 436/501; 435/7.1

(58) Field of Classification Search
None
See application file for complete search history.

(56) References Cited

U.S. PATENT DOCUMENTS

| | | |
|---|---|---|
| 4,036,945 A | 7/1977 | Haber |
| 4,331,647 A | 5/1982 | Goldenberg |
| 4,816,567 A | 3/1989 | Cabilly et al. |
| 4,946,778 A | 8/1990 | Ladner et al. |
| 5,591,828 A | 1/1997 | Bosslet et al. |

FOREIGN PATENT DOCUMENTS

EP 0 404 097 B1 9/1996

OTHER PUBLICATIONS

Krenacs et al., (Blood. Aug. 15, 1998.92;4:1308-1316).*
Dako, Dak-Pax 5 Monoclonal Mouse Anti-Human B-Cell-Specific Activator Protein Clone. Material Data Sheet. Jul. 10, 2008.*
Beaucage and Caruthers "Deoxynucleoside Phosphoramidites—A New Class of Key Intermediates for Deoxypolynucleotide Synthesis" *Tetrahedron Lett.* 22(20):1859-1869 (1981).
Bird et al. "Single-Chain Antigen-Binding Proteins" *Science* 242:423-426 (Oct. 21, 1988).
Bubendorf et al. "Tissue microarray (TMA) technology: miniaturized pathology archives for high-throughput in situ studies" *J. Pathol.* 195:72-79 (2001).
Clackson et al. "Making antibody fragments using phage display libraries" *Nature* 352:624-628 (Aug. 15, 1991).
Holliger et al. "'Diabodies': Small bivalent and bispecific antibody fragments" *Proc. Natl. Acad. Sci. USA* 90:6444-6448 (Jul. 1993).
Holmes et al. "Structural Consequences of Humanizing an Antibody" *J. Immunol.* 158:2192-2201 (1997).
Husson et al. "Gene expression profiling of follicular lymphoma and normal germinal center B cells using cDNA arrays" *Blood* 99:282-289 (2002).
Jones et al. "Replacing the complementarity-determining regions in a human antibody with those from a mouse" *Nature* 321:522-525 (May 29, 1986).
Kohler and Milstein "Continuous cultures of fused cells secreting antibody of predefined specificity" *Nature* 256:495-497 (Aug. 7, 1975).
Marks et al. "By-passing Immunization: Human Antibodies from V-gene Libraries Displayed on Phage" *J. Mol. Biol.* 222:581-597 (1991).
Matthes et al. "Simultaneous rapid chemical synthesis of over one hundred oligonucleotides on a microscale" *EMBO J.* 3(4):801-805 (1984).
Morrison et al. "Chimeric human antibody molecules: Mouse antigen-binding domains with human constant region domains" *Proc. Natl. Acad. Sci. USA* 81:6851-6855 (Nov. 1984).
Pack et al. "Improved Bivalent Miniantibodies, with Identical Avidity as Whole Antibodies, Produced by High Cell Density Fermentation of *Escherichia coli*" *Bio/Technology* 11:1271-1277 (Nov. 1993).
Riechmann et al. "Reshaping human antibodies for therapy" *Nature* 332:323-329 (Mar. 24, 1988).
Vaswani et al. "Humanized antibodies as potential therapeutic drugs" *Ann. Allergy Asthma Immunol.* 81:105-115 (Aug. 1998).
Went et al. "Marker Expression in Peripheral T-Cell Lymphoma: A Proposed Clinical-Pathologic Prognostic Score" *J. Clin. Oncol.* 24(16):2472-2479 (Jun. 1, 2006).

(Continued)

*Primary Examiner* — Cherie M Stanfield
(74) *Attorney, Agent, or Firm* — Finnegan, Henderson, Farabow, Garrett & Dunner, LLP

(57) ABSTRACT

The present invention relates to anti-human PAX 5 antibodies capable of binding to one or more epitopes located within the C-terminal regulatory domain of PAX 5. In particular the invention relates to an antibody, antigen binding fragment or recombinant protein thereof, which is capable of specific binding to an epitope located within the C-terminal fragment of human PAX 5 protein, wherein said epitope comprises from 3 to 17 amino acid residues of amino acid sequence GSPYYYSAAARGAAPPA (SEQ ID NO:2). The invention also relates to immunogenic peptide sequences for the production of the antibodies, diagnostic and therapeutic applications comprising using the antibodies and formulations comprising thereof.

27 Claims, No Drawings

(56) References Cited

OTHER PUBLICATIONS

Cozma et al., "B cell activator PAX5 promotes lymphomagenesis through stimulation of B cell receptor signaling," *J. Clinical Investigation* 117:2602-2610 (2007).

Feldman et al., "Diagnostic Uses of Pax5 Immunohistochemistry," *Adv. Anat. Pathol.*, 14:323-334 (2007).

International Search Report for PCT/DK2009/000156 mailed Dec. 2, 2009.

Jensen et al., "The utility of PAX5 immunohistochemistry in the diagnosis of undifferentiated malignant neoplasms," *Modern Pathology* 20:871-877 (2007).

Krenacs et al., "Transcription Factor B-cell-Specific Activator Protein (BSAP) Is Differentially Expressed in B Cells and in Subsets of B-Cell Lymphomas," *Blood* 92:1308-1316 (1998).

Mullighan et al., "Genome-wide analysis of genetic alterations in acute lymphoblastic leukaemia," *Nature* 446:758-764 (2007).

Pasqualucci et al., "Hypermutation of multiple proto-oncogenes in B-cell diffuse large-cell lymphomas," *Nature* 412:341-346 (2001).

Rehg et al., "Utility of AntiPax5 in the Diagnosis of Lymphoproliferative Disorders and Neoplasis in Mice," *Comparative Medicine* 58:246-252 (2008).

Tiacci et al., "PAX5 Expression in Acute Leukemias: Higher B-Lineage Specificity Than CD79a and Selective Association with t(8;21)-Acute Myelogenous Leukemia," *Cancer Research* 64:7399-7404 (2004).

Torlakovic et al., "The Value of Anti-PAX-5 Immunostaining in Routinely Fixed and Paraffin-Embedded Sections," *American Journal of Surgical Pathology* 26:1343-1350 (2002).

Willmann et al., "Pax5 immunostaining in paraffin-embedded sections of canine non-Hodgkin lymphoma: A novel canine pan pre-B- and B-cell marker," *Veterinary Immunology and Immunopathology* 128:359-365 (2009).

* cited by examiner

SEQUENCE LISTING

```
<160> NUMBER OF SEQ ID NOS: 27

<210> SEQ ID NO 1
<211> LENGTH: 391
<212> TYPE: PRT
<213> ORGANISM: Homo sapiens

<400> SEQUENCE: 1

Met Asp Leu Glu Lys Asn Tyr Pro Thr Pro Arg Thr Ser Arg Thr Gly
1               5                   10                  15

His Gly Gly Val Asn Gln Leu Gly Gly Val Phe Val Asn Gly Arg Pro
            20                  25                  30

Leu Pro Asp Val Val Arg Gln Arg Ile Val Glu Leu Ala His Gln Gly
        35                  40                  45

Val Arg Pro Cys Asp Ile Ser Arg Gln Leu Arg Val Ser His Gly Cys
    50                  55                  60

Val Ser Lys Ile Leu Gly Arg Tyr Tyr Glu Thr Gly Ser Ile Lys Pro
65                  70                  75                  80

Gly Val Ile Gly Gly Ser Lys Pro Lys Val Ala Thr Pro Lys Val Val
                85                  90                  95

Glu Lys Ile Ala Glu Tyr Lys Arg Gln Asn Pro Thr Met Phe Ala Trp
            100                 105                 110

Glu Ile Arg Asp Arg Leu Leu Ala Glu Arg Val Cys Asp Asn Asp Thr
        115                 120                 125

Val Pro Ser Val Ser Ser Ile Asn Arg Ile Ile Arg Thr Lys Val Gln
    130                 135                 140

Gln Pro Pro Asn Gln Pro Val Pro Ala Ser Ser His Ser Ile Val Ser
145                 150                 155                 160

Thr Gly Ser Val Thr Gln Val Ser Ser Val Ser Thr Asp Ser Ala Gly
                165                 170                 175

Ser Ser Tyr Ser Ile Ser Gly Ile Leu Gly Ile Thr Ser Pro Ser Ala
            180                 185                 190

Asp Thr Asn Lys Arg Lys Arg Asp Glu Gly Ile Gln Glu Ser Pro Val
        195                 200                 205

Pro Asn Gly His Ser Leu Pro Gly Arg Asp Phe Leu Arg Lys Gln Met
    210                 215                 220

Arg Gly Asp Leu Phe Thr Gln Gln Leu Glu Val Leu Asp Arg Val
225                 230                 235                 240

Phe Glu Arg Gln His Tyr Ser Asp Ile Phe Thr Thr Thr Glu Pro Ile
                245                 250                 255

Lys Pro Glu Gln Thr Thr Glu Tyr Ser Ala Met Ala Ser Leu Ala Gly
            260                 265                 270

Gly Leu Asp Asp Met Lys Ala Asn Leu Ala Ser Pro Thr Pro Ala Asp
        275                 280                 285

Ile Gly Ser Ser Val Pro Gly Pro Gln Ser Tyr Pro Ile Val Thr Gly
    290                 295                 300
```

```
Arg Asp Leu Ala Ser Thr Thr Leu Pro Gly Tyr Pro Pro His Val Pro
305                 310                 315                 320

Pro Ala Gly Gln Gly Ser Tyr Ser Ala Pro Thr Leu Thr Gly Met Val
            325                 330                 335

Pro Gly Ser Glu Phe Ser Gly Ser Pro Tyr Ser His Pro Gln Tyr Ser
            340                 345                 350

Ser Tyr Asn Asp Ser Trp Arg Phe Pro Asn Pro Gly Leu Leu Gly Ser
        355                 360                 365

Pro Tyr Tyr Tyr Ser Ala Ala Ala Arg Gly Ala Ala Pro Pro Ala Ala
    370                 375                 380

Ala Thr Ala Tyr Asp Arg His
385                 390

<210> SEQ ID NO 2
<211> LENGTH: 17
<212> TYPE: PRT
<213> ORGANISM: Artificial Sequence
<220> FEATURE:
<223> OTHER INFORMATION: Immunogenic peptide sequence

<400> SEQUENCE: 2

Gly Ser Pro Tyr Tyr Tyr Ser Ala Ala Ala Arg Gly Ala Ala Pro Pro
1               5                   10                  15

Ala

<210> SEQ ID NO 3
<211> LENGTH: 8
<212> TYPE: PRT
<213> ORGANISM: Artificial Sequence
<220> FEATURE:
<223> OTHER INFORMATION: Sub-sequence of SEQ ID NO:2

<400> SEQUENCE: 3

Tyr Tyr Ser Ala Ala Ala Arg Gly
1               5

<210> SEQ ID NO 4
<211> LENGTH: 9
<212> TYPE: PRT
<213> ORGANISM: Artificial Sequence
<220> FEATURE:
<223> OTHER INFORMATION: Sub-sequence of SEQ ID NO:2

<400> SEQUENCE: 4

Gly Ser Pro Tyr Tyr Tyr Ser Ala Ala
1               5

<210> SEQ ID NO 5
<211> LENGTH: 8
<212> TYPE: PRT
<213> ORGANISM: Artificial Sequence
<220> FEATURE:
<223> OTHER INFORMATION: Sub-sequence of SEQ ID NO:2

<400> SEQUENCE: 5

Ala Arg Gly Ala Ala Pro Pro Ala
1               5

<210> SEQ ID NO 6
<211> LENGTH: 4
<212> TYPE: PRT
<213> ORGANISM: Artificial Sequence
<220> FEATURE:
<223> OTHER INFORMATION: Sub-sequence of SEQ ID NO:2
```

```
<400> SEQUENCE: 6

Ala Arg Gly Ala
1

<210> SEQ ID NO 7
<211> LENGTH: 4
<212> TYPE: PRT
<213> ORGANISM: Artificial Sequence
<220> FEATURE:
<223> OTHER INFORMATION: Sub-sequence of SEQ ID NO:2

<400> SEQUENCE: 7

Ala Ala Ala Arg
1

<210> SEQ ID NO 8
<211> LENGTH: 6
<212> TYPE: PRT
<213> ORGANISM: Artificial Sequence
<220> FEATURE:
<223> OTHER INFORMATION: Sub-sequence of SEQ ID NO:2

<400> SEQUENCE: 8

Tyr Tyr Tyr Ser Ala Ala
1               5

<210> SEQ ID NO 9
<211> LENGTH: 5
<212> TYPE: PRT
<213> ORGANISM: Artificial Sequence
<220> FEATURE:
<223> OTHER INFORMATION: Sub-sequence of SEQ ID NO:2

<400> SEQUENCE: 9

Tyr Tyr Tyr Ser Ala
1               5

<210> SEQ ID NO 10
<211> LENGTH: 6
<212> TYPE: PRT
<213> ORGANISM: Artificial Sequence
<220> FEATURE:
<223> OTHER INFORMATION: Sub-sequence of SEQ ID NO:2

<400> SEQUENCE: 10

Tyr Ser Ala Ala Ala Arg
1               5

<210> SEQ ID NO 11
<211> LENGTH: 18
<212> TYPE: PRT
<213> ORGANISM: Artificial Sequence
<220> FEATURE:
<223> OTHER INFORMATION: Immunogen

<400> SEQUENCE: 11

Gly Ser Pro Tyr Tyr Tyr Ser Ala Ala Ala Arg Gly Ala Ala Pro Pro
1               5                   10                  15

Ala Cys

<210> SEQ ID NO 12
<211> LENGTH: 7
<212> TYPE: PRT
<213> ORGANISM: Artificial Sequence
<220> FEATURE:
<223> OTHER INFORMATION: Sub-sequence of SEQ ID NO:2
```

```
<400> SEQUENCE: 12

Gly Ser Pro Tyr Tyr Ser
1               5

<210> SEQ ID NO 13
<211> LENGTH: 7
<212> TYPE: PRT
<213> ORGANISM: Artificial Sequence
<220> FEATURE:
<223> OTHER INFORMATION: SUB-sequence of SEQ ID NO:2

<400> SEQUENCE: 13

Ser Pro Tyr Tyr Tyr Ser Ala
1               5

<210> SEQ ID NO 14
<211> LENGTH: 7
<212> TYPE: PRT
<213> ORGANISM: Artificial Sequence
<220> FEATURE:
<223> OTHER INFORMATION: Sub-sequence of SEQ ID NO:2

<400> SEQUENCE: 14

Pro Tyr Tyr Tyr Ser Ala Ala
1               5

<210> SEQ ID NO 15
<211> LENGTH: 7
<212> TYPE: PRT
<213> ORGANISM: Artificial Sequence
<220> FEATURE:
<223> OTHER INFORMATION: Sub-sequence of SEQ ID NO:2

<400> SEQUENCE: 15

Tyr Tyr Tyr Ser Ala Ala Ala
1               5

<210> SEQ ID NO 16
<211> LENGTH: 7
<212> TYPE: PRT
<213> ORGANISM: Artificial Sequence
<220> FEATURE:
<223> OTHER INFORMATION: Sub-sequence of SEQ ID NO:2

<400> SEQUENCE: 16

Tyr Tyr Ser Ala Ala Ala Arg
1               5

<210> SEQ ID NO 17
<211> LENGTH: 6
<212> TYPE: PRT
<213> ORGANISM: Artificial Sequence
<220> FEATURE:
<223> OTHER INFORMATION: Sub-sequence of SEQ ID NO:2

<400> SEQUENCE: 17

Gly Ser Pro Tyr Tyr Tyr
1               5

<210> SEQ ID NO 18
<211> LENGTH: 6
<212> TYPE: PRT
<213> ORGANISM: Artificial Sequence
<220> FEATURE:
<223> OTHER INFORMATION: Sub-sequnce of SEQ ID NO:2

<400> SEQUENCE: 18
```

```
Ser Pro Tyr Tyr Tyr Ser
1               5

<210> SEQ ID NO 19
<211> LENGTH: 6
<212> TYPE: PRT
<213> ORGANISM: Artificial Sequence
<220> FEATURE:
<223> OTHER INFORMATION: Sub-sequence of SEQ ID NO:2

<400> SEQUENCE: 19

Pro Tyr Tyr Tyr Ser Ala
1               5

<210> SEQ ID NO 20
<211> LENGTH: 6
<212> TYPE: PRT
<213> ORGANISM: Artificial Sequence
<220> FEATURE:
<223> OTHER INFORMATION: Sub-sequnce of SEQ ID NO:2

<400> SEQUENCE: 20

Tyr Tyr Ser Ala Ala Ala
1               5

<210> SEQ ID NO 21
<211> LENGTH: 6
<212> TYPE: PRT
<213> ORGANISM: Artificial Sequence
<220> FEATURE:
<223> OTHER INFORMATION: Y/A substitution in SEQ ID NO:8

<400> SEQUENCE: 21

Ala Tyr Tyr Ser Ala Ala
1               5

<210> SEQ ID NO 22
<211> LENGTH: 6
<212> TYPE: PRT
<213> ORGANISM: Artificial Sequence
<220> FEATURE:
<223> OTHER INFORMATION: Y/A substitution in SEQ ID NO:8

<400> SEQUENCE: 22

Tyr Ala Tyr Ser Ala Ala
1               5

<210> SEQ ID NO 23
<211> LENGTH: 6
<212> TYPE: PRT
<213> ORGANISM: Artificial Sequence
<220> FEATURE:
<223> OTHER INFORMATION: Y/A substitution in SEQ ID NO:8

<400> SEQUENCE: 23

Tyr Tyr Ala Ser Ala Ala
1               5

<210> SEQ ID NO 24
<211> LENGTH: 6
<212> TYPE: PRT
<213> ORGANISM: Artificial Sequence
<220> FEATURE:
<223> OTHER INFORMATION: Y/A substitution in SEQ ID NO:8

<400> SEQUENCE: 24

Tyr Tyr Tyr Ala Ala Ala
```

```
<210> SEQ ID NO 25
<211> LENGTH: 6
<212> TYPE: PRT
<213> ORGANISM: Artificial Sequence
<220> FEATURE:
<223> OTHER INFORMATION: A/G substitution in SEQ ID NO:8

<400> SEQUENCE: 25

Tyr Tyr Tyr Ser Gly Ala
1               5

<210> SEQ ID NO 26
<211> LENGTH: 6
<212> TYPE: PRT
<213> ORGANISM: Artificial Sequence
<220> FEATURE:
<223> OTHER INFORMATION: A/G substitution in SEQ ID NO:8

<400> SEQUENCE: 26

Tyr Tyr Tyr Ser Ala Gly
1               5

<210> SEQ ID NO 27
<211> LENGTH: 6
<212> TYPE: PRT
<213> ORGANISM: Artificial Sequence
<220> FEATURE:
<223> OTHER INFORMATION: Y/A substitution in a sub-sequence of SEQ ID
      NO:2

<400> SEQUENCE: 27

Ala Tyr Ser Ala Ala Ala
1               5
```

PAX 5 MONOCLONAL ANTIBODY

CROSS-REFERENCE TO RELATED APPLICATIONS

This application is a U.S. national stage entry under 35 U.S.C. §371 of International Application Number PCT/DK2009/000156, filed 25 Jun. 2009, which claims priority to Danish Patent Application Number PA 2008 00903, filed 30 Jun. 2008, and which also claims the benefit of U.S. Provisional Application No. 61/076,793 filed 30 Jun. 2008. Each of the aforementioned applications is incorporated herein by reference in its entirety.

FIELD OF INVENTION

The present invention relates to an antibody capable of binding to an epitope located in the C-terminal part of human PAX 5 protein and uses thereof for diagnostic and therapeutic applications.

BACKGROUND OF INVENTION

The transcription factor PAX 5 (BSAP) is essential for commitment of lymphoid progenitors to the B lymphocyte lineage. PAX 5 fulfils a dual role by repressing B lineage 'inappropriate' genes and simultaneously activating B lineage-specific genes. This transcriptional reprogramming restricts the broad signaling capacity of uncommitted progenitors to the B cell pathway, regulates cell adhesion and migration, induces V(H)-DJ(H) recombination, facilitates (pre-)B cell receptor signaling and promotes development to the mature B cell stage. Conditional PAX 5 inactivation in early and late B lymphocytes revealed an essential role for PAX 5 in controlling the identity and function of B cells throughout B lymphopoiesis. PAX 5 has also been implicated in human B cell malignancies, as it is deregulated by chromosomal translocations in a subset of acute lymphoblastic leukemias and non-Hodgkin lymphomas.

PAX 5 and Myc are the only 2 transcription factors consistently overexpressed in human follicular lymphoma cells compared with their putative normal counterparts, germinal center B cells (Mikkola I., et al., Blood, 99:282-289, 2002). Similarly, in DLBCLs, MYC and PAX 5 are the only 2 transcription factor-encoding genes with high frequencies of hypermutations (Pasqualucci, L., et al. 2001). Mutations in PAX 5 were also found, albeit with lower frequency, in Burkitt lymphomas with translocated Myc. Importantly, PAX 5 mutations cluster in regulatory sequences surrounding exon 1B, suggestive of its overexpression. Overall, high levels of PAX 5 protein have been reported in almost all non-Hodgkin lymphomas, but in very few acute leukemias (Krenas, L., et. al. 1998). Genetic data also support the involvement of PAX 5 in lymphomagenesis (Mullighan, et al., 2007; Cozma et al., 2007).

Use of anti-PAX 5 immunostaining in the diagnosis of pre-B acute lymphostatic leukemia and classic Hodkin lymphoma versus ALCL of T and "null" cell type was estimated to be very valuable. It was also useful in differential diagnosis between lymphoplasmatic lymphoma and plasmacytoma. Thus, it has been shown that even though there is an excellent correlation between CD20 and PAX 5 expression, anti-PAX 5 immunostaining exceeds the specificity and sensitivity of CD20 immunostaining because of PAX 5 earlier expression in B-cell differentiation and it is possible to detect all committed B cells, including classic Hodgkin lymphoma (Torlakovic E., et al., 2002).

REFERENCES

Cozma, D.; Yu, D.; Hodawadekar, S.; Azvolinsky, A.; Grande, S.; Tobias, J. W.; Metzgar, M. H.; Paterson, J.; Erikson, J.; Marafioti, T.; Monroe, J. G.; Atchison, M. L.; Thomas-Tikhonenko, A. B cell activator PAX5 promotes lymphomagenesis through stimulation of B cell receptor signaling. *J. Clin. Invest* 117: 2602-2610, 2007.

Mullighan, C. G.; Goorha, S.; Radtke, I.; Miller, C. B.; Coustan-Smith, E.; Dalton, J. D.; Girtman, K.; Mathew, S.; Ma, J.; Pounds, S. B.; Su, X.; Pui, C.-H.; Relling, M. V.; Evans, W. E.; Shurtleff, S. A.; Downing, J. R.: Genome-wide analysis of genetic alterations in acute lymphoblastic leukaemia. *Nature* 446: 758-764, 2007

Krenas, L., et. al. Transcription factor B-cell-specific activator protein (BSAP) is differentially expressed in B cells and in subsets of B-cell lymphomas. *Blood* 92:1308-1316, 1998

Pasqualucci, L.; Neumeister, P.; Goossens, T.; Nanjangud, G.; Chaganti, R. S. K.; Kuppers, R.; Dalla-Favera, R.: Hypermutation of multiple proto-oncogenes in B-cell diffuse large-cell lymphomas. *Nature* 412: 341-346, 2001.

Torlakovic, E., Torlakovich, G., Nguyen, P. L., Brunning R. D., Delabie, J. The value of anti-PAX 5 immunostaining in routinely fixed and parapffin-embedded sections. *Am. J. Surg. Pathol.* 261:1342-1350, 2002

SUMMARY OF INVENTION

The present invention relates to novel anti-human PAX 5 antibodies capable of binding to one or more epitopes located within the C-terminal regulatory domain of PAX 5 protein. The antibodies can be advantageously used for various research, diagnostic and/or therapeutic applications.

Antibodies of the invention are capable of binding to one or more epitopes located in the C-terminal part of the PAX 5 polypeptide comprising amino acid residues numbered 359 to 391 according to SEQ ID NO:1 (amino acid sequence of human PAX 5 protein). This part of PAX 5 is of major importance for the protein function: it participates in regulation of transcriptional activity of genes implicated in differentiation of B-cells, e.g. CD19, CD20, LEF-1, blk and/or mb-1 of the Ig genes. The antibody binding to PAX 5 may affect transcriptional activity and thus influence physiological effects depending on this activity. This makes antibodies of the invention to be a potential tool for therapeutic applications.

The antibodies are specific for PAX 5 protein i.e they do not bind other members of the PAX family, i.e. PAX 9. The antibodies possess a surprisingly higher affinity for PAX 5 protein than some other currently commercially available anti-PAX 5 antibodies. Both features make the antibody to be a beneficial both for research and diagnostic, e.g lymphoproliferative disorders.

Accordingly, a first aspect of the invention is an antibody, antigen binding fragment or recombinant protein thereof, which is capable of specific binding to an epitope located within the C-terminal fragment of human PAX 5 protein comprising amino acid residues numbered 359 to 391 according to SEQ ID NO:1, wherein said epitope comprises from 3 to 17 amino acid residues of amino acid sequence GSPYYYSAAARGAAPPA (SEQ ID NO:2). Amino acid sequence GSPYYYSAAARGAAPPA (SEQ ID NO: 2) corresponds to a fragment of SEQ ID NO:1 comprising amino acid residues 367 to 383.

In another aspect the invention relates to an isolated peptide sequence consisting of at maximum 25 consecutive amino acid residues comprising SEQ ID NO: 2 or a fragment of SEQ ID NO:2, for example one or more of the following subsequences of SEQ ID NO: 2: YYSAAARG (SEQ ID NO: 3), GSPYYYSAA (SEQ ID NO:4), ARGAAPPA (SEQ ID NO: 5), ARGA (SEQ ID NO: 6), AAAR (SEQ ID NO: 7), YYYSAA (SEQ ID NO: 8), YYYSA (SEQ ID NO. 9), YSAAAR (SEQ ID NO: 10), GSPYYYS (SEQ ID NO: 12), SPYYYSA (SEQ ID NO: 13), PYYYSAA (SEQ ID NO: 14), YYYSAAA (SEQ ID NO: 15), YYSAAAR (SEQ ID NO: 16), GSPYYY (SEQ ID NO: 17), SPYYYS (SEQ ID NO: 18), PYYYSA (SEQ ID NO: 19), or YYSAAA (SEQ ID NO: 20). The peptide sequence may be useful as immunogen for the production of an antibody of the invention. Accordingly, use of an isolated peptide sequence comprising at maximum 25 amino acid residues comprising SEQ ID NO: 2 or a subsequence thereof, for the production of an antibody capable of binding to an epitope located in the C-terminal part of human PAX-5 protein comprising amino acid residues numbered 359 to 391 according to SEQ ID NO:1, wherein the epitope comprises from 3 to 17 amino acid residues of amino acid sequence GSPYYYSAAARGAAPPA (SEQ ID NO:2) is another aspect of the invention.

In another aspect the invention relates to use of the antibodies of the invention for the detection of human PAX 5 protein in a biological sample in vitro, e.g. a tissue sample. The use may be related to research, diagnostic or therapy, e.g. to diagnostic of a lymphoproliferative disorder, e.g. different types of lymphoma, or to monitoring the progression of a lymphoproliferative disease in a patient, to evaluating the efficacy of a therapeutic treatment of a patient having a lymphoproliferative disease, to selecting a therapeutic treatment for a patient having a lymphoproliferative disease, etc.

In another aspect the invention relates to therapeutic applications of antibodies of the invention, in particular to pharmaceutical compositions comprising thereof and their use for treatment of lymphoproliferative disorders.

DETAILED DESCRIPTION OF THE INVENTION

1. Antibody

One aspect of the invention relates to an antibody, antigen binding fragment or recombinant protein thereof, which is capable of specific binding to an epitope located within the C-terminal fragment of human PAX 5 protein comprising amino acid residues numbered 359 to 391 according of SEQ ID NO:1, wherein said epitope comprises from 3 to 17 amino acid residues of amino acid sequence GSPYYYSAAARGAAPPA (SEQ ID NO:2).

Abbreviations for amino acids as used in herein are in accordance with the recommendations in the IUPAC-IUB Joint Commission on Biochemical Nomenclature Eur. J. Biochem, 1984, vol. 184, pp 9-37. Throughout the description and claims the one letter code for natural amino acids are used. Where the L or D form has not been specified it is to be understood that the amino acid in question has the natural L form, cf. Pure & Appl. Chem. Vol. (56(5) pp 595-624 (1984) or the D form, so that the peptides formed may be constituted of amino acids of L form, D form, or a sequence of mixed L forms and D forms.

By the term "antibody" is meant an immunoglobulin molecule whose basic building block, the immunoglobulin fold or domain, is used in various forms in many molecules of the immune system and other biological recognition systems. A typical immunoglobulin has four polypeptide chains, containing an antigen binding region known as a variable region and a non-varying region known as the constant region.

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light chain variable domain is aligned with the variable domain of the heavy chain. Particular amino acid residues are believed to form an interface between the light and heavy chain variable domains.

Depending on the amino acid sequences of the constant domain of their heavy chains, immunoglobulins can be assigned to different classes. There are at least five (5) major classes of immunoglobulins: IgA, IgD, IgE, IgG and IgM, and several of these may be further divided into subclasses (isotypes), e.g. IgG-1, IgG-2, IgG-3 and IgG-4; IgA-1 and IgA-2. The heavy chains found in different immunoglobulins belong to five different classes termed according the letters of Greek alphabet α, δ, ε, γ and μ. The type of heavy chain present defines the class of antibody; these chains are found in IgA, IgD, IgE, IgG, and IgM antibodies, respectively. The light chains of antibodies can be assigned to one of two clearly distinct types, called kappa (κ) and lambda (λ) based on the amino sequences of their constant domain. The subunit structures and three-dimensional configurations of different classes of immunoglobulins are well known.

The term "variable" in the context of variable domain of antibodies, refers to the fact that certain portions of the variable domains differ extensively in sequence among antibodies. The variable domains are for binding and determine the specificity of each particular antibody for its particular antigen. However, the variability is not evenly distributed through the variable domains of antibodies. It is concentrated in three segments called complementarity determining regions (CDRs) also known as hypervariable regions both in the light chain and the heavy chain variable domains.

The more highly conserved portions of variable domains are called the framework (FR)—The variable domains of native heavy and light chains each comprise four FR regions, largely a adopting a [beta]-sheet configuration, connected by three CDRs, which form loops connecting, and in some cases forming part of, the [beta]-sheet structure. The CDRs in each chain are held together in close proximity by the FR regions and, with the CDRs from the other chain, contribute to the formation of the antigen-binding site of antibodies. The constant domains are not involved directly in binding an antibody to an antigen, but exhibit various effector functions, such as participation of the antibody in antibody-dependent cellular toxicity.

Antibodies of the present invention thus can be in any of a variety of forms, including a whole immunoglobulins, antibody fragments, single chain antibodies which includes the variable domain complementarity determining regions (CDR), and the like forms, all of which fall under the broad term "antibody", as used herein.

The term "antigen binding fragment" refers to an antibody fragment or portion of a full-length antibody, generally the variable region. Examples of antigen binding fragments fragments of an antibody include Fab, Fab', F(ab') 2 and Fv fragments. Papain digestion of antibodies produces two identical antigen binding fragments, called the Fab fragment, each with a single antigen binding site, and a residual "Fc" fragment, so-called for its ability to crystallize readily. Pepsin treatment yields an F(ab') 2 fragment that has two antigen binding fragments that are capable of cross-linking antigen, and a residual other fragment (which is termed pFc'). Additional fragments can include diabodies, linear antibodies, single-chain antibody molecules, and multispecific antibodies formed from antibody fragments. As used herein, "antigen binding fragment" with respect to antibodies, refers to Fv, F(ab) and F(ab')2 fragments.

Some types of antibody fragments which are included in the scope of the invention are defined as follows:

(1) Fab is the fragment that contains a monovalent antigen-binding fragment of an antibody molecule. A Fab fragment can be produced by digestion of whole antibody with the enzyme papain to yield an intact light chain and a portion of one heavy chain.

(2) Fab' is the fragment of an antibody molecule can be obtained by treating whole antibody with pepsin, followed by reduction, to yield an intact light chain and a portion of the heavy chain. Two Fab' fragments are obtained per antibody molecule.

Fab' fragments differ from Fab fragments by the addition of a few residues at the carboxyl terminus of the heavy chain CH1 domain including one or more cysteines from the antibody hinge region.

(3) (Fab')$_2$ is the fragment of an antibody that can be obtained by treating whole antibody with the enzyme pepsin without subsequent reduction (4) F(ab')2 is a dimer of two Fab' fragments held together by two disulfide bonds. Fv is the minimum antibody fragment that contains a complete antigen recognition and binding site. This region consists of a dimer of one heavy and one light chain variable domain in a tight, non-covalent association (VH-VL dimer). It is in this configuration that the three CDRs of each variable domain interact to define an antigen binding site on the surface of the VH-VL dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

(5) Single chain antibody ("SCA"), defined as a genetically engineered molecule containing the variable region of the light chain, the variable region of the heavy chain, linked by a suitable polypeptide linker as a genetically fused single chain molecule. Such single chain antibodies are also referred to as "single-chain Fv" or "sFv" antibody fragments. Generally, the Fv polypeptide further comprises a polypeptide linker between the VH and VL domains that enables the sFv to form the desired structure for antigen binding. For a review of sFv see Pluckthun in The Pharmacology of Monoclonal Antibodies 113: 269-315 Rosenburg and Moore eds. Springer-Verlag, NY1 1994. Methods for producing sFvs are described, for example, by Whitlow, et al., 1991, In: Methods: A Companion to Methods in Enzymology, 2:97;

Another form of an antibody fragment is a peptide coding for a single complementarity-determining region (CDR). CDR peptides ("minimal recognition units") are often involved in antigen recognition and binding. CDR peptides can be obtained by cloning or constructing genes encoding the CDR of an antibody of interest. Such genes are prepared, for example, by using the polymerase chain reaction to synthesize the variable region from RNA of antibody-producing cells. See, for example, Larrick, et al., Methods: a Companion to Methods in Enzymology, Vol. 2, page 106 (1991).

The term "diabodies" refers to a small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, e.g., EP 404,097; or Hollinger et al., Proc. Natl. Acad. Sci. USA 90: 6444-6448 (1993).

Antigen binding fragments of the invention may be as small as 3 amino acids, 4 amino acids, 5 amino acids, 6 amino acids, 7 amino acids, 8 amino acids, 9 amino acids, about 12 amino acids, about 15 amino acids, about 18 amino acids, about 21 amino acids, about 25 amino acids, about 30 amino acids or more. The term "about" in the present context encompass antigen fragments that are 1 to 3 amino acid residues longer than the predetermined fragment of the range. In general, an antibody fragment of the invention can have any upper size limit so long as it is has similar or immunological properties relative to antibody that specifically binds to an epitope comprising at least three amino acid residues of amino acid sequence GSPYYYSAAARGAAPPA (SEQ ID NO: 2). Accordingly, the term "antibody" in its broad meaning also relates to antigen binding fragments and the term is thus interchangeably used herein with the term "antigen binding fragment" (of the antibody).

An antigen molecule (in the present context means is PAX 5 protein) may contain a number of the same or different antigenic determinants to which individual antibodies are made and bind to. The smallest unit (antigenic determinant) to which an antibody can be made is about three to six amino acid residues. This smallest antigenic determinant is termed "epitope". Antibodies can bind to conformational epitopes (conformational epitopes are interchangeably termed herein as non-linear epitopes) formed due folding of the protein molecule or linear epitopes represented by linear amino acid sequences which are fragments of the protein molecule.

In one embodiment the invention relates to an antibody which is capable of binding to a conformational epitope, in another embodiment the invention relates to an antibody which is capable of binding to a linear epitope. In particular, an antibody of the invention is capable of binding to an epitope comprising at least three amino acid residues of amino acid sequence GSPYYYSAAARGAAPPA (SEQ ID NO: 2). The at least tree amino acid residues of may be any amino acid residues of this amino acid sequence. The term "at least" means that an epitope to which the antibody of the invention is capable to binds to may consist of three or more amino acid residues. For example, an epitope of the invention may comprise from 3 to 17 amino acid residues, such as from 3 to 16, 15, 14, 13, 12, 11, 10, 9, 8, 7, 6, 5 or 4. In one embodiment the amino acid residues are the amino acid residues of SEQ ID NO:2. In one embodiment the amino acid residues making up an epitope of the invention are consecutive residues of SEQ ID NO:2, in another embodiment some of the amino acid residues are consecutive and some of the amino acid residues are partly scattered within the SEQ ID NO:2, in another embodiment the amino acid residues are scattered within the SEQ ID NO:2. In another embodiment the epitope may comprise three or more residues of SEQ ID NO:2 (consecutive and/or scattered) for example 4, 5, 6, 7, 8, 9, 10, and comprise amino acid residues of the C-terminal fragment of PAX 5 outside SEQ ID NO:2, e.g. one or more residues of the fragment comprising amino acid residues numbered 359 to 366 and/or amino acid residues numbered 384 to 391 according to SEQ ID NO:1, or, in some embodiment, amino acid residues located in the other parts of PAX 5 protein. Non-limited examples of subsequences of SEQ ID NO:2 involved in formation of an epitope of the invention may be sequence YYSAAARG (SEQ ID NO: 3), GSPYYYSAA (SEQ ID NO:4), ARGAAPPA (SEQ ID NO: 5), ARGA (SEQ ID NO: 6), AAAR (SEQ ID NO: 7), YYYSAA (SEQ ID NO: 8), YYYSA (SEQ ID NO. 9), YSAAAR (SEQ ID NO: 10), GSPYYYS (SEQ ID NO: 12), SPYYYSA (SEQ ID NO: 13), PYYYSAA (SEQ ID NO: 14), YYYSAAA (SEQ ID NO: 15), YYSAAAR (SEQ ID NO: 16), GSPYYY (SEQ ID NO: 17), SPYYYS (SEQ ID NO: 18), PYYYSA (SEQ ID NO: 19), or YYSAAA (SEQ ID NO: 20). In one preferred embodiment the epitope may comprise amino acid residues of SEQ ID NO: 8, in another preferred embodiment the epitope may comprise amino acid residues of SEQ ID NO: 13; in another preferred embodiment the epitope may comprise amino acid residues of SEQ ID NO:14; in another preferred embodiment the epitope may comprise amino acid residues of SEQ ID NO: 15; in another preferred embodiment the epitope may comprise amino acid residues of SEQ ID NO: 20.

In one embodiment the epitope may comprise at least one amino residue Y of SEQ ID NO: 2, i.e. residue $Y^{370}$, $Y^{371}$ or $Y^{372}$ (the numbering is according to SEQ ID NO:1). In another embodiment the epitope may comprise two Y residues of SEQ ID NO:2, e.g. $Y^{370}$ and $Y^{371}$, $Y^{370}$ and $Y^{372}$, or $Y^{371}$ and $Y^{372}$. In one preferred embodiment the epitope comprises $Y^{370}$ residue. In other preferred embodiments the epitope may comprise amino acid residue $Y^{370}$ and residues S and/or A of SEQ ID NO: 2, e.g. $S^{373}$ and/or $A^{374}$. In one embodiment residues S and/or Y are not phosphorylated. In one embodiment the epitope may comprise at least one P and/or G residue, e.g. $P^{369}$, $G^{367}$, $G^{378}$. In one embodiment the antibody binds to an epitope on human PAX protein comprising amino acid residue $Y^{370}$ and one or more of the following residues $P^{369}$, $Y^{370}$, $Y^{371}$, $Y^{372}$, $S^{373}$, $A^{374}$, $A^{375}$.

The invention relates to both polyclonal and monoclonal antibodies which are capable of specific binding to one or more epitopes described herein. In one embodiment the antibody is a polyclonal antibody. In another embodiment the antibody is a monoclonal antibody. The antibody according to invention may also be a human or humanized antibody. The polyclonal antibody may be e.g. rabbit, goat, swine, chicken antibody. The monoclonal antibody may be e.g. mouse, rabbit, rat, hamster antibody In one preferred embodiment the monoclonal antibody is a monoclonal antibody. Some nonlimited examples of mouse monoclonal antibodies that binds to the epitope(s) of the invention are described in Examples.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional polyclonal antibody preparations that typically include different antibodies directed against different determinants (epitopes), each monoclonal antibody is directed against a single determinant on the antigen. In additional to their specificity, the monoclonal antibodies are advantageous in that they are synthesized by the hybridoma culture, uncontaminated by other immunoglobulins. The modifier "monoclonal" indicates the character of the antibody indicates the character of the antibody as being obtained from a substantially homogeneous population of antibodies, and is not to be construed as requiring production of the antibody by any particular method.

The monoclonal antibodies herein may include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or sub-class, as well as fragments of such antibodies, so long as they exhibit the desired biological activity (U.S. Pat. No. 4,816,567); Morrison et al., 1984, Proc Natl Acad Sci 81: 6851-6855.

The term "polyclonal antibody" relates to a mixture of immunoglobulin molecules produced against a specific antigen molecule each recognizing a different epitope on this antigen.

Methods of in vitro and in vivo manipulation of monoclonal antibodies are well known to those skilled in the art. For example, the monoclonal antibodies to be used in accordance with the present invention may be made by the hybridoma method first described by Kohler and Milstein, 1975, Nature 256, 495-7, or may be made by recombinant methods, e.g., as described in U.S. Pat. No. 4,816,567. The monoclonal antibodies of the present invention may also be isolated from phage antibody libraries using the techniques described in Clackson et al., 1991, Nature 352: 624-628, as well as in Marks et al., 1991, J Mol Biol 222: 581-597. Another method involves humanizing a monoclonal antibody by recombinant means to generate antibodies containing human specific and recognizable sequences. See, for review, Holmes, et al., 1997, J Immunol 158:2192-2201 and Vaswani, et al., 1998, Annals Allergy, Asthma & Immunol 81:105-115.

As mentioned above, the invention contemplates human and humanized forms of non-human (e.g. murine) antibodies. Such humanized antibodies are chimeric immunoglobulins, immunoglobulin chains or fragments thereof (such as Fv, Fab, Fab', F(ab')2 or other antigen-binding subsequences of antibodies) that contain a minimal sequence derived from non-human immunoglobulin, such as the epitope recognising sequence. For the most part, humanized antibodies are human immunoglobulins (recipient antibody) in which residues from a complementary determining region (CDR) of the recipient are replaced by residues from a CDR of a nonhuman species (donor antibody) such as mouse, rat or rabbit having the desired specificity, affinity and capacity. Humanized antibody(es) containing a minimal sequence(s) of antibody(es) of the invention, such as a sequence(s) recognising the epitope(s) described herein, is a preferred embodiment of the invention. In some embodiments, the invention relates to humanized forms of mouse anti-human PAX 5 monoclonal antibodies described herein.

In some instances, Fv framework residues of the human immunoglobulin are replaced by corresponding non-human residues. Furthermore, humanized antibodies may comprise residues that are found neither in the recipient antibody nor in the imported CDR or framework sequences. These modifications are made to further refine and optimize antibody performance. In general, humanized antibodies will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details, see e.g. Jones et al., 1986, Nature 321, 522-525; or Reichmann et al., 1988, Nature 332, 323-329.

Antibodies capable of binding to one or more epitopes described above are characterized in that they have a very specific biding capacity to human PAX 5 protein and do not bind or have a much lower capacity of binding to the other members of the Pax family of transcription factors e.g. human PAX 2 or PAX 8 proteins. Thus, the antibodies described have a high specificity for human PAX 5 protein.

The antibodies of the invention may in some embodiments be able to modulate the functional activity of PAX 5 protein due to the fact that the epitope for antibody binding is located in the trans-activation domain of PAX 5 or in the nearby area to this domain.

Accordingly, the invention in some embodiments the invention relates to an PAX 5 antibody, that is capable of modulating biological function of PAX 5 protein in connection with regulation of activity of genes associated with lymphoid cell proliferation and differentiation, in particular lymphoid cell proliferation and differentiation, and cancer disease. The term "modulating" means both enhancing the activity of PAX 5 as transcriptional factor and inhibiting PAX 5 activity as transcriptional factor. Thus, in one embodiment the antibody may be a PAX 5 activating antibody, in another embodiment the antibody may be a PAX 5 inhibiting antibody.

2. Antibody Production

The preparation of polyclonal antibodies is well-known to those skilled in the art. See, for example, Green et al. 1992. Production of Polyclonal Antisera, in: Immunochemical Protocols (Manson, ed.), pages 1-5 (Humana Press); Coligan, et al., Production of Polyclonal Antisera in Rabbits, Rats Mice and Hamsters, in: Current Protocols in Immunology, section 2.4.1.

The preparation of monoclonal antibodies likewise is conventional. See, for example, Kohler & Milstein, Nature, 256: 495-7 (1975); Coligan, et al., sections 2.5.1-2.6.7; and Harlow, et al., in: Antibodies: A Laboratory Manual, page 726, Cold Spring Harbor Pub. (1988). Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan, et al., Production of Polyclonal Antisera in Rabbits, Rats Mice and Hamsters, in: Current Protocols in Immunology sections 2.7.1-2.7.12.

Methods of in vitro and in vivo manipulation of monoclonal antibodies are well known to those skilled in the art. For example, the monoclonal antibodies to be used in accordance with the present invention may be made by the hybridoma method first described by Kohler and Milstein, 1975, Nature 256, 495-7, or may be made by recombinant methods, e.g., as described in U.S. Pat. No. 4,816,567. The monoclonal antibodies for use with the present invention may also be isolated from phage antibody libraries using the techniques described in Clackson et al., 1991, Nature 352: 624-628, as well as in Marks et al., 1991, J Mol Biol 222: 581-597. Another method involves humanizing a monoclonal antibody by recombinant means to generate antibodies containing human specific and recognizable sequences. See, for review, Holmes, et al., 1997, J Immunol 158:2192-2201 and Vaswani, et al., 1998, Annals Allergy, Asthma & Immunol 81:105-115.

Methods of making antibody fragments are also known in the art (see for example, Harlow and Lane, Antibodies: A Laboratory Manual, Cold Spring Harbor Laboratory, NY, 1988, incorporated herein by reference). Antibody fragments of the present invention can be prepared by proteolytic hydrolysis of the antibody or by expression in *E. coli* of DNA encoding the fragment. Antibody fragments can be obtained by pepsin or papain digestion of whole antibodies conventional methods. For example, antibody fragments can be produced by enzymatic cleavage of antibodies with pepsin to provide a 5S fragment denoted F(ab')2—This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, in U.S. Pat. No. 4,036,945 and U.S. Pat. No. 4,331,647. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody. For example, Fv fragments comprise an association of VH and VL chains. This association may be noncovalent or the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow, et al., 1991, In: Methods: A Companion to Methods in Enzymology, 2:97; Bird et al., 1988, Science 242:423-426; U.S. Pat. No. 4,946,778; and Pack, et al., 1993, BioTechnology 11:1271-77.

The antibodies may also be produced in vivo by the individual to be treated, for ex*ample, by administering an immunogenic fragment according to the invention to said individual. Accordingly, the present invention further relates to a vaccine comprising an immunogenic fragment described above.

Thus, the generation of antibodies of the invention may be achieved by any standard methods in the art for producing polyclonal and/or monoclonal antibodies described above wherein an antigen comprising an epitope comprising at least three consecutive amino acid residues described above may be used.

A method for producing an antibody of the invention said method comprising a step of using an immunogenic fragment of human PAX 5 protein comprising amino acid residues constituting epitope(s) described above, or a synthetic amino acid sequence corresponding to this fragment, is another aspect of the invention.

3. Antigenic Amino Acid Sequences

In one embodiment an immunogenic amino acid sequence suitable for the production of an antibody of the invention may be a peptide sequence comprising of at most 25 consecutive amino acid residues comprising amino acid sequence GSPYYYSAAARGAAPPA (SEQ ID NO: 2) or a subsequence of this sequence, e.g. YYSAAARG (SEQ ID NO: 3), GSPYYYSAA (SEQ ID NO:4), ARGAAPPA (SEQ ID NO: 5), ARGA (SEQ ID NO: 6), AAAR (SEQ ID NO: 7), YYYSAA (SEQ ID NO: 8), YYYSA (SEQ ID NO. 9), YSAAAR (SEQ ID NO: 10), GSPYYYS (SEQ ID NO: 12), SPYYYSA (SEQ ID NO: 13), PYYYSAA (SEQ ID NO: 14), YYYSAAA (SEQ ID NO: 15), YYSAAAR (SEQ ID NO: 16), GSPYYY (SEQ ID NO: 17), SPYYYS (SEQ ID NO: 18), PYYYSA (SEQ ID NO: 19), or YYSAAA (SEQ ID NO:

20). In one preferred embodiment the peptide may comprise SEQ ID NO: 8, in another preferred embodiment the peptide may comprise SEQ ID NO: 13; in another preferred embodiment the peptide may comprise SEQ ID NO:14; in another preferred embodiment the peptide may comprise SEQ ID NO: 15; in another preferred embodiment the peptide may comprise SEQ ID NO: 20.

In one preferred embodiment the immunogentic sequence may comprise at least one amino residue Y and a sequence of tree or more consecutive amino acid residues of SEQ ID NO: 2. for example a sequence selected from YYSA, YSAA, GSPY, YYYS or SPYY. In another preferred embodiment the immunogenic peptide sequence may comprise at least one acid residue Y, at least one residue S and three or more consecutive amino acid residues of SEQ ID NO: 2. In another preferred embodiment the immunogenic peptide sequence may comprise sequence YYYSA (SEQ ID NO:9) and two or more consecutive amino acid residues of SEQ ID NO: 2.

In one embodiment the immunogenic peptide sequence may comprise a sequence from 6 to 17 amino acid residues, such as 10, 11, 12, 13, 14, 15 or 16 amino acid residues, wherein the sequence is a subsequence of SEQ ID NO:2.

In another embodiment the peptide sequence may consists of 6 or 7 amino acid residues, e.g. such as 6 amino acid peptide sequences YYYSAA (SEQ ID NO: 8) or YYSAAA (SEQ ID NO: 20), or 7 amino acid peptide sequences SPYYYSA (SEQ ID NO: 13), PYYYSAA (SEQ ID NO: 14) or YYYSAAA (SEQ ID NO: 15). In another embodiment the peptide sequence may consist of 17 amino acid residues, e.g. GSPYYYSAAARGAAPPA (SEQ ID NO: 2).

Where nothing is specified it is to be understood that the C-terminal amino acid of a peptide of the invention exists as the free carboxylic acid. However, the C-terminal amino acid of an immunogenic peptide of the invention may be the amidated derivative.

Where nothing else is stated the N-terminal amino acid of a peptide comprises a free amino-group.

The peptide fragments comprising immunogenic sequences of the invention may comprise or consist of variants of said sequences.

"Variants of peptide sequences" means that the peptides may be modified, for example by substitution of one or more of the amino acid residues. Both L-amino acids and D-amino acids may be used. Other modification may comprise derivatives such as esters, sugars, etc. Examples are methyl and acetyl esters. Polymerisation such as repetitive sequences or attachment to various carriers are well-known in the art, e.g. lysine backbones, such as lysine dendrimers carrying 4 peptides, 8 peptides, 16 peptides, or 32 peptides. Other carriers may be protein moieties, such as bovine serum albumin (BSA), or lipophilic dendrimers, or micelle-like carriers formed by lipophilic derivatives, or starburst (star-like) carbon chain polymer conjugates, or ligand presenting assembly (LPA) based on derivatives of diethylaminomethane.

Variants of the peptide fragments according to the invention may comprise, within the same variant, or fragments thereof or among different variants, or fragments thereof, at least one substitution, such as a plurality of substitutions introduced independently of one another. Variants of the complex, or fragments thereof may thus comprise conservative substitutions independently of one another, wherein at least one glycine (G) of said variant, or fragments thereof is substituted with an amino acid selected from the group of amino acids consisting of A, V, L, and I, and independently thereof, variants, or fragments thereof, wherein at least one alanine (A) of said variants, or fragments thereof is substituted with an amino acid selected from the group of amino acids consisting of G, V, L, and I, and independently thereof, variants, or fragments thereof, wherein at least one valine (V) of said variant, or fragments thereof is substituted with an amino acid selected from the group of amino acids consisting of G, A, L, and I, and independently thereof, variants, or fragments thereof, wherein at least one leucine (L) of said variant, or fragments thereof is substituted with an amino acid selected from the group of amino acids consisting of G, A, V, and H, and independently thereof, variants, or fragments thereof, wherein at least one isoleucine (I) of said variants, or fragments thereof is substituted with an amino acid selected from the group of amino acids consisting of G, A, V and L, and independently thereof, variants, or fragments thereof wherein at least one aspartic acids (D) of said variant, or fragments thereof is substituted with an amino acid selected from the group of amino acids consisting of E, N, and Q, and independently thereof, variants, or fragments thereof, wherein at least one aspargine (N) of said variants, or fragments thereof is substituted with an amino acid selected from the group of amino acids consisting of D, E, and Q and independently thereof, variants, or fragments thereof, wherein at least one glutamine (Q) of said variants, or fragments thereof is substituted with an amino acid selected from the group of amino acids consisting of D, E, and N, and wherein at least one phenylalanine (F) of said variants, or fragments thereof is substituted with an amino acid selected from the group of amino acids consisting of Y, W, H, P, and preferably selected from the group of amino acids consisting of Y and W, and independently thereof, variants, or fragments thereof, wherein at least one tyrosine (Y) of said variants, or fragments thereof is substituted with an amino acid selected from the group of amino acids consisting of F, W, H, P, preferably an amino acid selected from the group of amino acids consisting of F and W, and independently thereof, variants, or fragments thereof, wherein at least one arginine (R) of said fragment is substituted with an amino acid selected from the group of amino acids consisting of K and H, and independently thereof, variants, or fragments thereof, wherein at least one lysine (K) of said variants, or fragments thereof is substituted with an amino acid selected from the group of amino acids consisting of R and H, and independently thereof, variants, or fragments thereof, and independently thereof, variants, or fragments thereof, and wherein at least one proline (P) of said variants, or fragments thereof is substituted with an amino acid selected from the group of amino acids consisting of F, Y, W, and His, and independently thereof, variants, or fragments thereof, wherein at least one cysteine (C) of said variants, or fragments thereof is substituted with an amino acid selected from the group of amino acids consisting of D, E, K, R, H, N, Q, S, T, and Y.

In one embodiment the term "variants" may be understood as amino acid sequences gradually differing from the preferred predetermined sequence, as the number and scope of insertions, deletions and substitutions including conservative substitutions increase. This difference is measured as a reduction in homology between the pre-determined sequence and the variant.

The peptide sequences described above are intended for the production of antibodies capable of binding to the epitope described herein. However, in some embodiments the sequences may be use as modulators of activity of PAX 5 as transcriptional activator as they can compete for the binding sites in PAX 5 itself or other biological molecules which the epitope of the invention may be involved in functional interaction.

Peptide sequences as described above may be prepared by many commercial manufactures, e.g. GenScrip, Pepscan Presto BV, Lonza etc. Alternatively, the peptide sequences of the present invention may be prepared by any conventional synthetic methods, recombinant DNA technologies, enzymatic cleavage of full-length PAX 5 protein or a combination of said methods known to a skilled in the art. For example, suitable recombinant procedure may be selected form the described in e.g. Sambrook et al., Molecular cloning: A Laboratory manual. 2 rd ed., CSHL Press, Cold Spring Harbor, N.Y., 1989; Beaucage and Caruthers, 1981, Tetrahedron Lett. 22:1859-1869; Matthes et al., 1984, EMBO J. 3:801-805; A method for synthetic production of peptides may be found in Synthetic Peptides: A User's Guide (Advances in Molecular Biology), Grant G. A. ed., Oxford University Press, 2002, or in: Pharmaceutical Formulation: Development of Peptides and Proteins, Frokjaer and Hovgaard eds., Taylor and Francis, 1999.

4. Use of Antibodies

Antibodies of the invention may be advantageously used in different research, diagnostic, and therapeutic applications. Some non-limited embodiments of use of the antibodies are described below.

In one embodiment the antibodies may be used for the detection of human PAX 5 protein in a biological sample in vitro.

"Biological sample" refers to a sample of biological material obtained from a subject, preferably a human subject, including a tissue, tissue sample, or cell sample (e.g., a tissue biopsy, for example, an aspiration biopsy, a brush biopsy, a surface biopsy, a needle biopsy, a punch biopsy, an excision biopsy, an open biopsy, an incision biopsy or an endoscopic biopsy), tumor, tumor sample, or biological fluid (e.g., blood, serum, lymph, spinal fluid).

As used herein, a "tissue sample" refers to a portion, piece, part, segment, or fraction of a tissue which is obtained or removed from an intact tissue of a subject, preferably a human subject. For example, tissue samples can be obtained from the pancreas, stomach, liver, secretory gland, bladder, lung, skin, prostate gland, breast ovary, cervix, uterus, brain, eye, connective tissue, bone, muscles, vasculature, etc. The biological sample may be a tumor sample (e.g., a tumor biopsy). As used herein, a "tumor sample" refers to a portion, piece, part, segment, or fraction of a tumor, for example, a tumor which is obtained or removed from a subject (e.g. removed or extracted from a tissue of a human subject). A tumor sample can be obtained, for example, from a lung carcinoma, a colon carcinoma, a cervical carcinoma, an adenocarcinoma, a melanoma, a leukemia, a lymphoma, a glioma, a neuroblastoma, a retinoblastoma, and a sarcoma. In one embodiment, the tumor sample is obtained from a primary tumor (e.g., is a primary tumor sample). In another embodiment, the tumor sample is obtained metastatic lesion (e.g., is a metastatic lesion sample). As defined herein, a "primary tumor" is a tumor appearing at a first site within the subject and can be distinguished from a "metastatic tumor" which appears in the body of the subject at a remote site from the primary tumor. As used herein, a "metastatic tumor" is a tumor resulting from the dissemination of cells from a primary tumor by the lymphatics or blood vessels or by direct extension through serum-containing or serum-producing cavities or other spaces.

As used herein, the term "isolated", when used in the context of a biological sample, is intended to indicate that the biological sample has been removed from the subject. In one embodiment, a biological sample comprises a sample which has been isolated from a subject and is subjected to a method of the present invention without further processing or manipulation subsequent to its isolation. In another embodiment, the biological sample can be processed or manipulated subsequent to being isolated and prior to being subjected to a method of the invention. For example, a sample can be refrigerated (e.g., stored at 4° C.), frozen (e.g., stored at −20° C., stored at −135° C. frozen in liquid nitrogen, or cryopreserved using any one of many standard cryopreservation techniques known in the art). Furthermore, a sample can be purified subsequent to isolation from a subject and prior to subjecting it to a method of the present invention. As used herein, the term "purified" when used in the context of a biological sample, is intended to indicate that at least one component of the isolated biological sample has been removed from the biological sample such that fewer components, and consequently, purer components, remain following purification.

Concerning tissue or tumor samples (termed generally "histological samples"), the samples can in general be divided in two categories: (a) preparations comprising fresh tissues and/or cells, which generally are not fixed with aldehyde-based fixatives, and (b) fixed and, optionally, paraffin embedded tissue specimens, often archived material.

In one embodiment of the invention the histological sample is of (a) category, in another embodiment the histological sample is of (b) category Preparation of histological sample for different in vitro immunoanalyses and immunoassays are very well known in the art, e.g. methods of fixing and embedding tissue specimens are known, for example, alcohol fixation and formalin-fixation and subsequent paraffin embedding (FFPE), protein immunodetection techniques using tissue samples e.g. immunohistochemistry, are also well known. In a prepared tissue sample PAX 5 protein may be detected by an antibody described above by using any suitable immunohistochemistry assay (the assay may be found e.g. in J. A. Kiernan, Histological and Histochemical Methods: Theory and Practice, 4th edition, Cold Spring Harbor Laboratory Pr, 2008).

Immunochemical evaluation of PAX 5 protein expression in a biological sample may be advantageously used for diagnostic applications.

In one embodiment the invention relates to a method of diagnosis of a cancer in a human subject, said method comprising a step of contacting a tissue sample isolated from this subject with an antibody of the invention, or with an agent comprising an antibody of the invention, such that the presence of PAX 5 polypeptide is detected in the biological sample, thereby diagnosing the cancer wherein expression of PAX 5 is indicative of the disease.

Diagnostic methods of the present invention may involve a quantitative determination of the level of expression of PAX 5 protein in the sample, i.e. measuring the amount of PAX 5 in the sample, or a qualitative determination i.e. determining the presence versus the absence of PAX 5 protein in the sample. Diagnostic methods of the present invention may also involve comparing the level of PAX 5 polypeptide in the sample with the level of PAX 5 polypeptide in a control sample, i.e. obtained from a subject who is not having the disease in question. As used herein, the phrase "comparing the level" includes evaluating, balancing or contrasting the amount or presence of PAX 5 protein in a first sample (e.g., a test sample) with the amount or presence of PAX 5 protein in a second sample (e.g., a control sample). In yet another embodiment, the diagnostic methods may further include the step of forming a prognosis or forming a diagnosis and stratifying patients for appropriate therapy. The invention in one embodiment relates to a prognostic method for determining whether a subject is at risk for developing cancer said method comprising a step of involve contacting a biological sample obtained from the subject with an antibody of the invention, or an agent comprising the antibody, such that the presence of PAX 5 polypeptide is detected in the biological sample, and associating the presence or absence of PAX 5 protein in the sample with the risk for developing the disease, e.g. cancer, in that subject. As used herein, a subject "at risk for developing a disease, e.g. cancer" includes a subject which has been determined to have a higher probability of developing cancer when compared to an average representative of the population. A subject's "risk of developing cancer" can be based on an analysis of empirical criteria or on a person's pedigree.

Antibodies described herein are capable of binding to minor amounts of PAX 5 in cells and therefore they are suitable for detection of minor amounts of the protein in cells which makes these antibodies a valuable tool in cancer diagnostics and cancer therapy of the diseases wherein particular PAX 5 expression patterns are diagnostic criteria of the disease. For example, the antibodies of the invention may be used in a method of diagnosing a lymphoma another lymphoproliferative disorder, wherein the disorder is associated with abnormal expression of PAX 5 in a patient.

Accordingly, in one embodiment the invention relates to a method of diagnosing a lymphoma in a patient, wherein said method comprises a step of immunological detection of PAX 5 protein in vitro in a sample obtained from said patient by using an antibody of the invention. Antibodies of the invention may be useful for diagnosis of Chronic lymphocytic leukemia/Small lymphocytic lymphoma,
B-cell prolymphocytic leukemia,
Lymphoplasmacytic lymphoma/Waldenström macroglobulinemia,
Splenic marginal zone lymphoma,
Plasma cell neoplasms,
Plasma cell myeloma,
Plasmacytoma,
Monoclonal immunoglobulin deposition diseases,
Heavy chain diseases,
Extranodal marginal zone B cell lymphoma (MALT lymphoma),
Nodal marginal zone B cell lymphoma,
Follicular lymphoma,
Mantle cell lymphoma,
Diffuse large B cell lymphoma,
Mediastinal (thymic) large B cell lymphoma,
Intravascular large B cell lymphoma,
Primary effusion lymphoma,
Burkitt lymphoma/leukemia,
Lymphomatoid granulomatosis,
T cell prolymphocytic leukemia,
T cell large granular lymphocytic leukemia,
Aggressive NK cell leukemia,
Adult T cell leukemia/lymphoma,
Extranodal NK/T cell lymphoma, nasal type,
Enteropathy-type T cell lymphoma,
Hepatosplenic T cell lymphoma,
Blastic NK cell lymphoma,
Mycosis fungoides/Sezary syndrome,
Primary cutaneous CD30-positive T cell lymphoproliferative disorders,
Primary cutaneous anaplastic large cell lymphoma,
Lymphomatoid papulosis,
Angioimmunoblastic T cell lymphoma,
Peripheral T cell lymphoma, unspecified or,
Anaplastic large cell lymphoma.

In other embodiments the antibodies may be used in methods of selecting patient for a particular therapeutic treatment, e.g. in case a patient is diagnosed having a disease selected from any of the above, or in methods of evaluating the efficacy of therapeutic treatment of these diseases, or in methods of monitoring the status of these diseases, in case the evaluation of PAX 5 expression/presence in biological samples may be indicative of the efficacy or status.

Embodiments the invention also include use of the antibodies in
a method for diagnosing for distinguishing pre-B acute lymphostatic leukemia from Anastatic Large Cell Lymphoma (ALCL) of T and "null" cell type comprising evaluating the level of PAX 5 protein in a biological sample in vitro; and
a method for distinguishing classic Hodkin lymphoma from Anastatic Large Cell Lymphoma (ALCL) of T and "null" cell type comprising evaluating the level of PAX 5 protein in a biological sample in vitro.

As mentioned, the above described diagnostic methods may employ any conventional immunohistochemical staining techniques. For example, the tissue sample may be fixed in formalin, B-5 or other standard histological preservatives, dehydrated and embedded in paraffin as is routine in any hospital pathology laboratory. Sections may be cut from the paraffin and mounted on glass slides. The cellular antigen can then be detected and localized either by exposure to labelled antibody and a labelled secondary antibody. Alternatively, cytological preparations may be used. For example, cells from the tissue sample may be fixed on a slide, typically by exposure to formalin in a buffer at physiologic pH followed by suspension in acetone and pelleting onto gelatin-coated slides by centrifugation. The presence of PAX 5 may then be detected, either by exposure to labelled antibody or by exposure to unlabelled antibody and a labelled secondary antibody. The amount of PAX 5 in the sample is directly proportional to the amount of bound label.

Kit-of-Parts Comprising Antibodies

In another aspect, the invention relates to a kit-of-parts for detecting the presence of PAX 5 in a biological sample, said kit-of-parts comprising a labeled or non-labeled antibody of the invention. The term "labeled", with regard to the antibody, relates both to an antibody physically, e.g. via chemical bond, linked to a detectable substance, and antibody indirectly labeled with a detectable substance, wherein said detectable substance is not physically linked to the antibody. Examples of indirect labeled antibodies include a primary antibody associated with a secondary labeled with a detectable substance, e.g. a fluorescent substance, hapten, etc, In one embodiment, the kit further includes a means for determining the antibody bound to PAX 5 in the sample, e.g. secondary antibody, e.g. rabbit anti-mouse antibody in case the PAX 5 antibody is mouse monoclonal antibody. In yet another embodiment, the kit further includes a means for detection of secondary antibody. The kit may also comprise directions for use.

Compositions Comprising Antibodies

The antibodies of the invention may also be used in therapeutic applications, e.g. for treatment of lymphoproliferative disorders. Accordingly in another aspect the invention relates to a pharmaceutical composition comprising an antibody of the invention. In the present context the term "pharmaceutical composition" is used synonymously with the term "medicament".

The pharmaceutical composition of the invention may for example be used to inhibit proliferation of cancer cells and/or promote differentiation of cells in vitro or in vivo, e.g. to inhibit lymphoid cell proliferation or promote B-cells differentiation.

The composition is administered to a subject in vivo or to be used in vitro contains an effective amount of one or more of the compounds described above in combination with pharmaceutically acceptable additives. Such medicament may suitably be formulated for oral, percutaneous, intramuscular, intravenous, intracranial, intrathecal, intracerebroventricular, intranasal or pulmonal administration.

Strategies in formulation development of medicaments and compositions based on the compounds of the present invention generally correspond to formulation strategies for any other protein-based drug product. Potential problems and the guidance required to overcome these problems are dealt with in several textbooks, e.g. "Therapeutic Peptides and Protein Formulation. Processing and Delivery Systems", Ed. A. K. Banga, Technomic Publishing AG, Basel, 1995.

The antibodies of the present invention as medicament are sufficiently active, but in some embodiments the effect of the antibodies may be enhanced if the preparation further comprises pharmaceutically acceptable additives and/or carriers. Such additives and carriers will be known in the art. In some cases, it will be advantageous to include a compound, which promotes delivery of the active substance to its target.

EXAMPLES

The following is a description of non-limited examples of antibodies of the invention and their uses.

Example 1

Production of Antibody

Female F1 hybrids of NMRI and BALB/c mice were immunized with a synthetic peptide GSPYYYSAAAR-GAAPPAC (SEQ ID NO: 11) conjugated to KLH (Keyhole Limpet Hemocyanin). Mice were immunized three times at two weeks interval. Plasma from immunized mice was tested for positive reaction with PAX5 protein by ELISA and IHC.

Cell fusion was made, utilizing the spleenocytes from the immunized mice and an appropriate myeloma cell line (X63, NS-1, or an equivalent). Fusion was performed using PEG and fused cells were harvested in hypoxanthine, aminopterin, thymidine (HAT) containing medium which selectively allows growth of hybridomas. Viable hybridoma colonies were grown out in 24 well plates. After 2 weeks, supernatants were screened by ELISA testing and IHC. Positive cells are selected for further sub-cloning. Approved clones were sub-cloned by limited dilution. Sub-cloning is performed until all clones are ELISA-positive.

Two positive clones, A22D2 and B22D2, have been selected for epitope mapping analyses described in Example 4.

Example 2

Immunological Detection of PAX 5 in Tissue Samples by DAK-PAX 5 Antibody

Verification of diagnostic value of mAb DAK-PAX 5 in immunohistochemical (IHC) assays was performed on routinely formalin-fixed, paraffin-embedded specimens from patients with lymphoproliferative disorders.

Materials and Methods

Materials included 880 tissue specimens obtained from patients suffering from lymphoproliferative disorders with a verified diagnosis. The specimens were all formalin-fixed, paraffin-embedded archival material from the Registry of the Haematopathology Unit of Bologna University, which were assembled into 30 separate Tissue Micro Arrays (TMAs). The compositions of 29 of these TMAs (comprising 722 specimens) are indicated in the column "tumor type" in table 1. The remaining 158 specimens from Classic Hodgkin's Lymphoma patients were assembled into the last TMA (table 2).

TMAs were generated according to standard procedures, as described by Went et al. (J. Clin. Oncol. 16 (2006) 2472-2479), by punching tissue cylinders (1.0 mm in diameter) from marked areas of tissue blocks containing patient material. Punching and placing of tissue cylinders into recipient paraffin blocks was done by using a precision instrument as described by Bubendorf et al. (J Pathol 195 (2001) 72-79).

Four micrometer thick routine sections of TMA blocks were placed onto glass slides and dried for 1 h at 60° C. Sections were then de-waxed with Histoclear and rehydrated through ethanol/water dilutions, and subsequently subjected to antigen retrieval in 1 mM EDTA (pH 8.0) by microwaving (3 cycles of 5' each at 900 W).

De-masked sections were then incubated with primary antibodies at room temperature for 30' at following dilutions (DAK-PAX 5: 1:50; Clone 24/BD Bioscience Catalog No 610863 1:30). The alkaline anti-alkaline phosphatase complexes (APAAP) method and EnVision$^+$ System were alternatively used for antibody detection.

Optimal pretreatment regimens and dilutions for both antibodies, as used above, were selected after thoroughly conduction of chess board titration analysis on sections from both reactive tonsils and classical Hodgkin lymphoma samples. In particular, the following antigen retrieval media were tested in a microwave oven (3 cycles of 5' each at either 750 or 900 W): 1 mM EDTA (pH 8.0), 1 mM EDTA-NaOH solution (pH 9.0), and 0.01 M citrate buffer (pH 6.0). In addition, de-masking with 0.05% Protease XVI (Pronase E) for 5' at 37° C. was also tested. The antibodies were diluted 1:50-1:300 (DAK-PAX 5) and 1:10-1:150 (Clone 24/BD Bioscience Catalog No 610863). The optimal dilution for both was chosen based on the clear-cut reactivity of Hodgkin and Reed-Sternberg cells. In fact, the latter do usually express PAX 5 at a lower intensity than normal B-cells as described by Jensen et al. (Mod Pathol 20 (2007) 871-7). Reactive B-lymphocytes were still stained at the highest dilutions used.

A negative control antibody with matching isotype (IgG1—Dako code X0931) was incubated on control slides from the same TMA blocks at similar concentrations as both DAK-PAX 5 and Clone 24.

Washes between incubations were carried out in TBS with 0.05% Tween 20, pH 7.6, and sections were counterstained with Gill's or Mayer's haematoxylin depending on the detection system used (APAAP and Envision$^+$, respectively).

Immunohistochemical Analysis

Stained sections were independently evaluated by at least two experienced hematopathologists. Cases were considered positive if 30% or more of the tumor cells were stained with an antibody. The number of positive cells was estimated by each observer.

Results

Distribution of positive/negative cases of all Non-Classic Hodgkin's Lymphoma specimens are summarized in Table 1.

TABLE 1

Staining results obtained with IHC staining with DAK-PAX 5 and Clone 24 performed on 722 specimens of Non-Classic Hodgkin's Lymphoma cases, which were organized into 29 separate TMAs.

| TUMOR TYPE | No. of positive reacting cases with DAK-PAX 5/Total no. of evaluated cases | No. positive reacting cases with CLONE24/ Total no. of evaluated cases |
|---|---|---|
| Acute myeloid leukemia | 0/6 | 0/6 |
| Precursor B-lymphoblastic leukaemia/lymphoma | 6/6 | 6/6 |
| Precursor T-lymphoblastic leukaemia/lymphoma | 0/6 | 0/6 |
| Chronic myelogenous Leukaemia | 0/6 | 0/6 |
| Plasma cell myeloma | 0/6 | 0/6 |
| Reactive tonsil and lymph node | 28/28 | 28/28 |
| Follicular lymphoma | 41/41 | 41/41 |
| Hairy cell leukaemia | 6/6 | 6/6 |
| Splenic marginal zone lymphoma | 11/11 | 11/11 |
| Nodal marginal zone lymphoma | 12/12 | 12/12 |
| Mantle cell lymphoma | 66/66 | 66/66 |
| Chronic lymphocytic leukaemia/small lymphocytic lymphoma | 76/76 | 76/76 |
| Diffuse large B cell lymphoma | 127/127 | 127/127 |
| T cell rich large B cell lymphoma | 6/6 | 6/6 |
| Mediastinal large B cell lymphoma | 22/22 | 22/22 |
| Burkitt lymphoma | 30/30 | 30/30 |
| Atypical Burkitt lymphoma | 5/5 | 5/5 |
| Peripheral T cell lymphoma unspecified (PTCL/U) | 0/157 | 0/157 |
| Angioimmunoblastic T-cell lymphoma | 0/45 | 0/45 |
| Anplastic large cell lymphoma ALK+ | 0/27 | 0/27 |
| Anplastic large cell lymphoma ALK− | 1/18* | 1/18* |
| Mycosis fungoides | 0/5 | 0/5 |
| Extranodal Nk/T-cell lymphoma nasal-type | 0/1 | 0/1 |
| Hepatosplenic T-cell lymphoma | 0/1 | 0/1 |
| Subcutaneous panniculitis-like T-cell lymphoma | 0/1 | 0/1 |
| post transplant PTCL/U | 0/1 | 0/1 |
| Nodular lymphocyte predominant Hodgkin lymphoma | 6/6 | 6/6 |
| Post-transplant lymphoproliferative disorders | 23/30 | 23/30 |
| Neuroendocrine Carcinoma | 4/16 | 4/16 |

*Aberrant PAX 5 expression in one ALK− ALCL that—at molecular analysis—showed clonal T-cell receptor gamma gene rearrangement and polyclonal IgV$_H$ gene pattern.

When tested on the disease cases referenced in table 1, incubation with DAK-PAX 5 resulted in expected specific staining of lymphomas derived from pro-, pre-, and mature B cells, no staining in plasmas cell derived lymphomas (myelomas) and no staining of T-cell on Null-cell derived lymphomas. When comparisons were made (at optimal dilutions) between Clone 24 and DAK-PAX 5, they resulted in similar staining patterns in all instances. However, incubation with DAK-PAX 5 generally resulted in stronger specific staining of both pro-, pre-, and mature B cells.

Additionally, specific reactivity was observed in Hodgkin's and Reed-Sternberg cells (HRSCs) in most of the tested cases of Classic Hodgkin's Lymphoma cases (Table 2).

TABLE 2

Staining results obtained with IHC staining with DAK-PAX 5 and Clone 24 performed on 158 specimens of Classic Hodgkin's Lymphomas, which were organized into 26 separate TMAs.

| Classical Hodgkin Lymphoma | Positive[a] | Weakly positive[b] | Doubtful[c] | Negative[e] |
|---|---|---|---|---|
| Dak-PAX 5 | 61/158 | 36/158 | 21/158 | 40/158 |
| Clone 24 | 15/158 | 36/158 | 33/158 | 74/158 |

[a]Positive: >30% neoplastic Hodgkin and Reed-Stenberg cells stained as intensively as normal B- lymphocytes.
[b]Weakly positive: >30% neoplastic Hodgkin and Reed-Sternberg cells stained at a lower intensity than normal B-lymphocytes.
[c]Doubtful: faintly-stained Hodgkin and Reed-Sternberg cells in a percentage below the 30% cut-off value.
[e]Negative: no neoplastic Hodgkin and Reed-Sternberg cells stained, the internal controls (normal B-lymphocytes) being always strongly positive.

When comparisons were made (at optimal dilutions) between Clone 24 and DAK-PAX 5 a higher proportion of HRSCs in CHL cases stained positive (P<0.0001) and lower proportions were either doubtful (P=0.0996) or negative (P=0.0001) when stained with DAK-PAX 5 (all P values were obtained by using Fisher's Exact Test).

Conclusions

This example confirms the immunoreactivity of mAb DAK-PAX 5 in routinely fixed, paraffin-embedded lymphomas both derived from pro-, pre-, and mature B cells, and in HRSCs in CHL. This staining pattern, combined lack of immunostaining of lymphomas derived from plasma cells (myelomas), T-cell and Null-cells, verifies the diagnostic utility of DAK-PAX 5 in immunohistochemical (IHC) assays.

The observation of stronger specific staining of pro-, pre-, and mature B cells and in particular HRSCs in most CHL cases, without confounding background staining, may reduce the likelihood of a false negative diagnosis of CHL, when IHC assays to differentiate this disease from T-cell and Null-cell derived ALCL are conducted with mAb DAK-PAX 5.

Example 3

Comparison of Sensitivity of Different PAX 5 Antibodies for Detection of PAX 5 in IHC Material and Methods Formalin fixed paraffin embedded (FFPE) tonsil and Hodgkin's lymphoma tissue blocks were cut at 4-5 μm on a standard microtome and mounted on SuperFrost-plus glass slides, air dried at room temperature (20-25° C.) for one hour and placed at 60° C. for 1 hour. Sections were then deparaffinised in xylene and rehydrated though ethanol/water solutions. Subsequently sections were subjected to heat induced antigen retrieval using Dako EnVision™ FLEX target retrieval solution, low pH (Dako codes K8001/K8011) in a microwave oven (Whirlpool) at 750 W for 20 minutes. After boiling, sections were allowed to cool at room temperature for 20 minutes. Antigen retrieved sections were then incubated with either monoclonal mouse B-Cell Specific Activator Protein (BSAP), clone DAK-Pax5, monoclonal mouse PAX 5, clone 24 (BD Biosciences), rabbit monoclonal PAX5, clone BV6 (Abcam), rabbit polyclonal PAX 5 (Thermo scientific/NeoMarkers) at 3 μg/mL for 20 minutes. Immunereactions were detected with EnVision™ FLEX+, low pH (Dako Codes K8003/K8013) and EnVision™ Flex+ Rabbit Linker (Dako Code K8019) according to package inserts. The peroxidase reaction was developed with 3,3'diaminobenzidine tetrahydrocholoride (DAB+). Washes between incubations were carried out in TBS with Tween 20, pH 7.6 (Dako code S3006), and sections were counterstained in Mayer's haematoxylin. The concentration of the antibodies was determined by ELISA.

TABLE 3

| | Antibody description | | | | |
|---|---|---|---|---|---|
| Ab ID | Company | Clone | Isotype | Concentration | Immunogen/ epitope |
| 2362 | BD Biosciences | Mab 24 | IgG1 | 228 μg/ml | Human PAX 5 aa 151-306.(N- terminal) |
| 2367 | abcam | Rb—Mo BV6 | IgG | 11 μg/ml | A synthetic cyclic peptide corresponding to C terminal residues of PAX5. (C- terminal) |
| 2363 | Thermo scientific/ NeoMarkers | Rb-Pol | — | 87 μg/ml | A synthetic peptide derived from C-terminus of human PAX 5 protein. (C-terminal) |
| 2348 | Dako | Mab DAK-Pax5 | IgG1 | 170 μg/ml | Synthetic 17-meric peptide from the C-terminal inhibitory domain of the protein. (C terminal) |

Results and Conclusion

Initial testing demonstrated that Mab 2362, Mab 2363 and Mab 2348 are more sensitive than Mab 2367 with regard to detecting Reed Stenberg cells in Hodkins lymphoma and B-cells in tonsil tissue specimens. The ability of Mab 2362, Mab 2363 and Mab 2348 to detect Reed Sternberg cells in 4 different Hodkins lymphomas were compared and the results demonstrated that Mab 2348 and Mab 2363 are more sensitive than Mab 2362 (Table 2). Mab 2348 and Mab 2363 detected Reed Sternberg cells in 3 out of 4 cases of Hodkins lymphomas but the staining intensity of Reed Sternberg cells were much higher with Mab 2348 than with Mab 2363, indicating that Mab 2348 is more sensitive than Mab 2363 (Table 2).

TABLE 4

|  | Mab 2363 3 µg/mL | Mab 2362 3 µg/mL | Mab 2348 3 µg/mL |
|---|---|---|---|
| Hodkins lymphoma 1* | 3+ | 2 | 6+ |
| Hodkins lymphoma 2* | 0 | 0 | 0 |
| Hodkins lymphoma 3* | 1 | 1 | 2 |
| Hodkins lymphoma 4* | 2 | 2 | 6+ |

*Stained sections were evaluated in an IHC assay and scored based on staining intensity of Reed Sternberg cells in Hodkins lymphoma and rated on a scale of 0 to 6, with 0 representing no staining, 1 and 2 - weak staining, 3 and 4 - moderate staining, and 5 and 6 representing the strong staining.

Example 4

Epitope Mapping

To determine the epitopes for two new human PAX 5 monoclonal antibodies, A22D2 and B22D2, it was performed the epitope mapping analysis. A22D2 and B22D2 have been obtained as described in example 1.

Clones A22D2 and B22D2 were tested for reactivity with PAX protein by epitope mapping by probing a synthetic peptide "SPOT" array with primary antibody followed by visualization using an enzyme-labelled secondary antibody.

The linear size scan is the systematic screening of all possible overlapping peptides derived from the antigen sequence. The linear size scan allows the identification of the minimal stretch of amino acids reactive for the antibody.

In brief, solid phase synthesis of synthetic libraries of peptides on a chemically activated support like a cellulose membrane or a polystyrene pin/well is the sequential application of a small volume of Fmoc activated and side chain protected amino acid in a defined pattern.

The process involves repeated cycles of chemical coupling, washings to remove by-products from the coupling reaction, and the selective removal of the eventual amino-protecting group and until the desired peptide is assembled for the antibody. Each defined "SPOT" in the pattern carries a single and defined peptide sequence. The solid support is chemically blocked to inactivate excess reactive coupling groups. From washings to remove side chain protecting groups, the peptides are incubated with the antibody in evaluation, followed by washings and the incubation with an enzyme-labeled visualization antibody. The intensity from a time-controlled substrate reaction can be measured in a reader.

Table 4 below demonstrates results of the linear six scan reactivity of A22D2 and B22D2 antibodies. The reaction level was estimated and categorized as follows: "minus" is background staining, "+" is defined a marked reaction, "++" is defined a maximum reaction.

TABLE 4

| Amino acid Position | Amino acid Sequence | Reactivity A22D2 | Reactivity B22D2 |
|---|---|---|---|
| $G^{367}$-$S^{373}$ | GSPYYYS (SEQ ID NO: 12) | − | − |
| $S^{368}$-$A^{374}$ | SPYYYSA (SEQ ID NO: 13) | − | + |
| $P^{369}$-$A^{375}$ | PYYYSAA (SEQ ID NO: 14) | ++ | ++ |
| $Y^{370}$-$A^{376}$ | YYYSAAA (SEQ ID NO: 15) | ++ | ++ |
| $Y^{371}$-$R^{377}$ | YSAAAR (SEQ ID NO: 16) | − | − |
| $G^{367}$-$Y^{372}$ | GSPYYY (SEQ ID NO: 17) | − | − |
| $S^{368}$-$S^{373}$ | SPYYYS (SEQ ID NO: 18) | − | − |
| $P^{369}$-$A^{374}$ | PYYYSA (SEQ ID NO: 19) | − | − |
| $Y^{370}$-$A^{375}$ | YYYSAA (SEQ ID NO: 8) | ++ | ++ |
| $Y^{371}$-$A^{376}$ | YSAAA (SEQ ID NO: 20) | − | + |
| $Y^{372}$-$R^{377}$ | YSAAAR (SEQ ID NO: 10) | − | − |

The Alanine/Glycine replacement scan is the systematic screening of mutually sized sequences with the substitution of each residue for Alanine or Glycine, which allows the identification of amino acid residues that contribute to the binding epitope of an antibody.

Table 5 below demonstrates the results of the Alanine/Glycine replacement scan of sequence YYYSAA (SEQ ID NO: 8), and YYSAAA (SEQ ID NO: 20).

TABLE 5

| Amino acid Position | Amino acid Sequence | Reactivity A22D2 | Reactivity B22D2 |
|---|---|---|---|
| $A^{370}$ | AYYSAA (SEQ ID NO: 21) | − | − |
| $A^{371}$ | YAYSAA (SEQ ID NO: 22) | ++ | ++ |
| $A^{372}$ | YYASAA (SEQ ID NO: 23) | − | + |
| $A^{373}$ | YYYAAA (SEQ ID NO: 24) | + | ++ |
| $G^{374}$ | YYYSGA (SEQ ID NO: 25) | + | ++ |
| $G^{375}$ | YYYSAG (SEQ ID NO: 26) | ++ | ++ |
| $A^{376}$ | AYSAAA (SEQ ID NO: 27) | − | − |

The results of the epitope mapping shows that both monoclonal antibodies recognize the amino acid sequence $^{370}$YYYSAA$^{375}$, suggesting that the epitope in human PAX 5 protein for both A22D2 and B22D2 comprises at least some amino acid residues of this sequence. Within this sequence, residues Y371 and Y373 seem to be important for the antibody binding, Substitution of these residues with alanine (A) or glycine (G) led to decrease in antibody binding. Comparing the reactivity with the truncated 5-amino acid peptide, YYYSA, revealed that A376, the last residue of the sequence, is important for binding of antibody B22D2 than antibody A22D2, indicating that the antibodies may recognize slightly different epitopes or have different binding capacity.

A22D2 and B22D2 were also compared with PAX 5 polyclonal antibody Ab9600. For Ab9600 was defined that the epitope comprises the sequence $^{373}$YSAAAR$^{378}$ of PAX 5. In this case, substitutions with alanine or glycine at any positions abrogated binding. Thus, the results indicate that Ab9600 binds to a different epitope in PAX 5 compare to the epitopes defined for A22D2 and B22D2, although the epitopes of the antibodies are somehow overlapping.

Neither of antibodies B22D2 or A22D2 showed pronounced cross-reactivity to the other PAX protein family members. Lack of the cross-reactivity is an important feature of the antibodies qualifying them for use in a research, diagnostic, prognostic and therapeutic applications.

The invention claimed is:

1. An antibody, antigen binding fragment, or recombinant protein thereof which specifically binds to an epitope located within the C-terminal fragment of human PAX 5 protein, wherein the C-terminal fragment of human PAX 5 protein comprises amino acid residues 359 to 391 of SEQ ID NO:1, wherein the epitope comprises at least one amino acid residue Y selected from the group consisting of $Y^{370}$, $Y^{371}$ and $Y^{372}$ of SEQ ID NO:1.

2. The antibody, antigen binding fragment, or recombinant protein thereof according to claim 1, wherein the epitope comprises from 3 to 10 amino acid residues of amino acid sequence GSPYYYSAAARGAAPPA (SEQ ID NO:2).

3. The antibody, antigen binding fragment, or recombinant protein thereof according to claim 1, wherein the epitope comprises from 3 to 6 amino acid residues of amino acid sequence GSPYYYSAAARGAAPPA (SEQ ID NO:2).

4. The antibody, antigen binding fragment, or recombinant protein thereof according to claim 2, wherein the epitope comprises amino acid residues Y, S, and A.

5. The antibody, antigen binding fragment, or recombinant protein thereof according to claim 1, wherein the epitope is linear.

6. The antibody, antigen binding fragment, or recombinant protein thereof according to claim 1, wherein the epitope is non-linear.

7. The antibody, antigen binding fragment, or recombinant protein thereof according to claim 1, wherein the epitope comprises residue $Y^{370}$ of SEQ ID NO:1.

8. The antibody, antigen binding fragment, or recombinant protein thereof according to claim 7, wherein the epitope comprises a residue selected from $Y^{371}$ of SEQ ID NO:1 and $Y^{372}$ of SEQ ID NO:1.

9. The antibody, antigen binding fragment, or recombinant protein thereof according to claim 8, wherein the epitope comprises residue $Y^{372}$ of SEQ ID NO:1.

10. The antibody, antigen binding fragment, or recombinant protein thereof according to claim 8, wherein the epitope comprises residue $S^{373}$ of SEQ ID NO:1.

11. The antibody, antigen binding fragment, or recombinant protein thereof according to claim 8, wherein the epitope comprises residue $A^{374}$ of SEQ ID NO:1.

12. The antibody, antigen binding fragment, or recombinant protein thereof according to claim 8, wherein the epitope comprises residue $Y^{371}$ of SEQ ID NO:1.

13. The antibody, antigen binding fragment, or recombinant protein thereof according to claim 1, wherein the epitope comprises amino acid residues of amino acid sequence YYYSAA (SEQ ID NO: 8).

14. The antibody, antigen binding fragment, or recombinant protein thereof according to claim 1, wherein the antibody is a polyclonal antibody.

15. The antibody, antigen binding fragment, or recombinant protein thereof according to claim 1, wherein the antibody is a monoclonal antibody.

16. A composition comprising the antibody, antigen binding fragment, or recombinant protein thereof according to claim 1.

17. The composition according to claim 16, wherein the composition is a kit-of-parts for the detection of human PAX 5 protein in vitro.

18. The composition according to claim 16, wherein the composition is a pharmaceutical composition.

19. A method for the detection of human PAX 5 protein in a biological sample in vitro comprising contacting the sample with the antibody, antigen binding fragment, or recombinant protein thereof of claim 1 and detecting the presence of the antibody, antigen binding fragment, or recombinant protein thereof bound to the PAX 5 protein.

20. The method of claim 19, wherein the biological sample is a tissue or cell sample.

21. The method of claim 19, wherein the sample is a formalin-fixed and paraffin-embedded tissue sample.

22. A method of diagnosing a lymphoma in a patient, wherein said method comprises immunological detection of PAX 5 protein in a sample from said patient in vitro, the detection comprising using the antibody, antigen binding fragment, or recombinant protein thereof according to claim 1.

23. The method according to claim 22, wherein the lymphoma is selected from
Chronic lymphocytic leukemia/Small lymphocytic lymphoma,
B-cell prolymphocyte leukemia,
Lymphoplasmacytic lymphoma/Waldenström macroglobulinemia,
Splenic marginal zone lymphoma,
Plasma cell neoplasms,
Plasma cell myeloma,
Plasmacytoma,
Monoclonal immunoglobulin deposition diseases,
Heavy chain diseases,
Extranodal marginal zone B cell lymphoma (MALT lymphoma),
Nodal marginal zone B cell lymphoma,
Follicular lymphoma,
Mantle cell lymphoma,
Diffuse large B cell lymphoma,
Mediastinal (thymic) large B cell lymphoma,
Intravascular large B cell lymphoma,
Primary effusion lymphoma,
Burkitt lymphoma/leukemia,
Lymphomatoid granulomatosis,
T cell prolymphocyte leukemia
T cell large granular lymphocytic leukemia,
Aggressive NK cell leukemia,
Adult T cell leukemia/lymphoma,
Extranodal NK/T cell lymphoma, nasal type,
Enteropathy-type T cell lymphoma,
Hepatosplenic T cell lymphoma,
Blastic NK cell lymphoma,
Mycosis fungoides/Sezary syndrome,
Primary cutaneous CD30-positive T cell lymphoproliferative disorders
Primary cutaneous anaplastic large cell lymphoma,
Lymphomatoid papulosis,
Angioimmunoblastic T cell lymphoma,
Peripheral T cell lymphoma, unspecified, and
Anaplastic large cell lymphoma.

24. The method of claim 22, wherein the lymphoma is pre-B acute lymphostatic leukemia.

25. The method of claim 22, wherein the lymphoma is classic Hodgkin's lymphoma.

26. A method for determining the risk of development of a cancer in a subject, the method comprising immunologically detecting PAX 5 protein in a biological sample collected from said subject, determining the level of PAX 5 protein in the sample, and associating the presence or absence of PAX5 in the sample with the risk for developing cancer, wherein the immunological detecting comprises using the antibody, antigen binding fragment, or recombinant protein thereof according to claim 1.

27. A method of producing the antibody, antigen binding fragment, or recombinant protein thereof of claim 1, comprising using a peptide containing an amino acid sequence derived from the C-terminal fragment of human PAX 5 protein as an immunogen, wherein the C-terminal fragment of human PAX 5 protein comprises amino acid residues 359 to 391 of SEQ ID NO:1, wherein the peptide contains from 3 to 17 consecutive amino acid residues of amino acid sequence GSPYYYSAAARGAAPPA (SEQ ID NO:2), and wherein the 3 to 17 consecutive amino acid residues of SEQ ID NO:2 comprises at least one amino acid residue Y selected from the group consisting of residues 4, 5, and 6 of SEQ ID NO:2, corresponding to $Y^{370}$, $Y^{371}$, and $Y^{372}$ of SEQ ID NO:1.

* * * * *